US009499785B2

(12) United States Patent
Vassiliev et al.

(10) Patent No.: US 9,499,785 B2
(45) Date of Patent: Nov. 22, 2016

(54) ISOLATING A MAMMALIAN EMBRYONIC STEM CELL FROM A HOMOGENOUS PLURIPOTENT OUTGROWTH OF A MAMMALIAN PRE-IMPLANTATION EMBRYO

(75) Inventors: Ivan Vassiliev, Urrbrae (AU); Mark Brenton Nottle, Bibaringa (AU)

(73) Assignee: ICMSTEMCELL PTY LTD, Bibaringa, South Australia (AU)

( * ) Notice: Subject to any disclaimer, the term of this patent is extended or adjusted under 35 U.S.C. 154(b) by 66 days.

(21) Appl. No.: 12/446,801

(22) PCT Filed: Oct. 24, 2007

(86) PCT No.: PCT/AU2007/001619
§ 371 (c)(1),
(2), (4) Date: Apr. 23, 2009

(87) PCT Pub. No.: WO2008/049161
PCT Pub. Date: May 2, 2008

(65) Prior Publication Data
US 2010/0017899 A1    Jan. 21, 2010

(30) Foreign Application Priority Data
Oct. 24, 2006    (AU) .............................. 2006905889

(51) Int. Cl.
*C12N 15/00*    (2006.01)
*C12N 5/073*    (2010.01)
*C12N 5/0735*    (2010.01)

(52) U.S. Cl.
CPC ........... *C12N 5/0604* (2013.01); *C12N 5/0606* (2013.01); *C12N 2500/25* (2013.01); *C12N 2500/40* (2013.01); *C12N 2500/44* (2013.01); *C12N 2500/84* (2013.01); *C12N 2500/90* (2013.01); *C12N 2501/11* (2013.01); *C12N 2501/115* (2013.01); *C12N 2501/235* (2013.01); *C12N 2502/13* (2013.01)

(58) Field of Classification Search
CPC ............. C12N 5/0606; C12N 2501/115; C12N 2506/02; C12N 2501/11; C12N 5/0623; C12N 2502/02; C12N 5/0672; C12N 5/0678; C12N 5/068; C12N 2500/90; C12N 2500/84; C12N 5/0604
See application file for complete search history.

(56) References Cited

U.S. PATENT DOCUMENTS

| 5,905,042 | A | 5/1999 | Stice et al. | |
| 2004/0229350 | A1* | 11/2004 | Strelchenko et al. | 435/366 |
| 2004/0253721 | A1* | 12/2004 | Bongso et al. | 435/371 |
| 2005/0153444 | A1 | 7/2005 | Mandalam | |
| 2010/0138947 | A1 | 6/2010 | Vassiliev | |

FOREIGN PATENT DOCUMENTS

| WO | 9747734 A1 | 12/1997 |
| WO | 9827214 A1 | 6/1998 |
| WO | 2006036164 A1 | 4/2006 |

OTHER PUBLICATIONS

Thomson et al. Embryonic Stem Cell Lines Derived from Human Blastocysts, Science, 1998, vol. 282, pp. 1145-1147.*
Sotiropoulou et al. Characterization of the Optimal Culture Conditions for Clinical Scale Production of Human Mesenchymal Stem Cells. Stem Cells, 2006, vol. 24, pp. 462-471, originally pbulsihed on line Aug. 18, 2005.*
Amit et al. Clonally Derived Human Embryonic Stem Cell Lines Maintain Pluripotency and Proliferative Potential for Prolonged Periods of Culture Develop. Biol., vol. 227, pp. 271-278.*
Pelton et al. Transient pluripotent cell populations during primitive ectoderm formation: correlation of in vivo and in vitro pluripotent cell development. Journal of Cell Science, 2002, vol. 115, pp. 329-339.*
Nagy et al. Derivation of completely cell culture-derived mice from early-passage embryonic stem cells. PNAS, 1993, vol. 90, pp. 8424-8428.*
Campbell et al. Epiblast Cell Number and Primary Embryonic Stem Cell Colony Generation Are Increased by Culture of Cleavage Stage Embryos in Insulin. J. Reproduction Develop., 2013, vol. 59, pp. 131-138.*
Stern et al. The hypoblast (visceral endoderm): an evo-devo perspective. Development, 2012, vol. 139, pp. 1059-1069.*
Xu, Ren-He et al. Basic FGF and suppression of BMP signaling sustain undifferentiated proliferation of human ES cells. Nature Methods, 2005, vol. 2, pp. 185-190.*
Valbuena D et al. "Derivation and Characterization of Three New Spanish Human Embryonic Stem Cell Lines (VAL-3-4-5) on Human Feeder and in Serum-Free Conditions." Reproductive BioMedicine Online. vol. 13, No. 6. pp. 875-886. 2006.
Cheng, J. et al. "Improved Generation of C57BL/6J mouse embryonic stem cells in a defined serum-free media." Genesis. vol. 39, No. 100. pp. 100-104. 2004.
Klimanskaya I. et al. "Human Embryonic Stem Cells Derived Without Feeder Cells" Lancet. vol. 365, pp. 1636-1641. 2005.
Nichols J. et al."Derivation and Propagation of Embryonic Stem Cells in Serum- and Feeder-Free Culture." Methods in Molecular Biology. vol. 329. 2006.
Lee et al. "Establishment and Maintenance of Human Embryonic Stem Cell Lines on Human Feeder Cells Derived from Uterine Endometricum under Serum-Free Condition." Biology of Reproduction, Society for the Study of Reproduction, vol. 72, pp. 42-49. 2005.

(Continued)

*Primary Examiner* — Deborah Crouch
(74) *Attorney, Agent, or Firm* — Brown & Michaels, PC

(57) ABSTRACT

The present invention provides a method of isolating a pluripotent cell from a pre-implantation embryo without isolation of the pluripotent cells from other cells, the method including propagating a whole pre-implantation embryo including one or more pluripotent cells, embedded in a feeder cell layer and cultivated in a medium substantially free of serum, and isolating a pluripotent cell from the one or more pluripotent cells. The present invention also provides pluripotent cells generated by the method and uses thereof.

15 Claims, 16 Drawing Sheets

(56) References Cited

OTHER PUBLICATIONS

Stekelenburg-Hamers, A. et al. "Isolation and Characterization of Permanent Cell Lines From Inner Cell Mass Cells of Bovine Blastocysts." Molecular Reproduction and Development, vol. 40. No. 4, pp. 444-454. 1995.
Lee et al. "Serum Replacement With a Growth Factor-Free Synthetic Substance in Culture Medium Contributes to Effective Establishment of Mouse Embryonic Stem Cells of Various Origins." Fertility and Sterility, vol. 86. No. 5 pp. 1137-1145. 2006.
First et al. "Systems for Production of Calves From Cultured Bovine Embryonic Cells." Reproduction, Fertility and Development. vol. 6. No. 5. pp. 553-562. 1994.
Ilic et al. "Derivation of hESC From Intact Blastocysts." Current Protocols in Stem Cell Biology, Unit 1A.2, 2007, XP009137177.
Inzunza, J. et al. "Derivation of Human Embryonic Stem Cells Cell Lines in Serum Replacement Medium Using Postanatal Human Fibroblasts as Feeder Cells." Stem Cells. vol. 23. pp. 544-549. 2005.
Richoux et al., "Distribution of Fibronectins and Laminin in the Early Pig Embryo", The Anatomical Record, 223:72-81 (1989).
Talbot et al., "Culturing the Epiblast Cells of the Pig Blastocyst", In Vitro Cell. Dev. Biol., 9A: 543-554 (1993).
Stroband et al., "The Pig Blastocyst: its Ultrastructure and the Uptake of Protein Macromolecules", Cell Tissue Res 235: 347-356 (1984).
Richter, "The Importance of Growth Factors for Preimplantation Embryo Development and in-vitro Culture", Curr Opin Obstet Gynecol, 20: 292-304 (2008).
Mohr and Trounson, "Comparative Ultrastructure of Hatched Human, Mouse and Bovine Blastocysts", J. Reprod. Fert., 66: 499-504 (1982).
Buchwalaw et al., "Non-specific Binding of Antibodies in Immunohistochemistry: Fallacies and Facts", Scientific Reports, pp. 1-6 (2011).
Nadjicka and Hillman, "Ultrastructural Studies of the Mouse Blastocyst Substages", J. Embryol. exp. Morph., vol. 32:3, pp. 675-695 (1974).
Hogan and Tilly, "In vitro Development of Inner Cell Masses Isolated Immunosurgically from Mouse Blastocysts", J. Embryol. exp. Morph. vol. 45, pp. 93-105 (1978).
Talbot et al., "In vitro Pluripotency of Epiblasts Derived From Bovine Blastocysts", Molecular Reproduction and Development, 42: 35-52 (1995).
O'Rahilly and Muller, "Developmental Stages in Human Embryos", Carnegie Institution of Washington, Publication No. 637, pp. 17-20 (1987).
Thomson et al., "Isolation of a Primate Embryonic Stem Cell Line", Proc. Natl. Acad. Sci., vol. 92, pp. 7844-8748 (Aug. 1995).
http://www.ehd.org/virtual-human-embryo/intro.php?stage=2, saved on Oct. 24 and 27, 2014.
Gasser RF, 1975, "Atlas of human embryos", Hagerstown, Maryland: Harper and Row, chapter 1, pp. 1-4, http://www.ehd.org/pdf/gasser/Gasser-ch1.pdf.
Tachibana et al., 2012, "Generation of chimeric rhesus monkey", Cell, 148: 285-295.
Hanna JH et al., 2010, "Pluripotency and cellular reprogramming: facts, hypothesis, unresolved issues", Cell, 143: 508-525.
Ware CB et al., 2014, "Derivation of naïve human embryonic stem cells", PNAS USA 111: 4484-4489.
Vassiliev I et al., 2010, "In Vitro and In Vivo Characterization of Putative Porcine Embryonic Stem Cells", Cellular Reprogramming, 12: 223-230.
http://www.rndsystems.com/molecule_group.aspx?g=796, saved on Oct. 24, 2014.
Hebert et al., 1991, "mRNA localization studies suggest that murine FGF-5 plays a role in gastrulation", Development 112: 407-415.
Chazaud et al., 2006, "Early Lineage Segregation between Epiblast and Primitive Endoderm in Mouse Blastocysts through the Grb2-MAPK Pathway", Developmental Cell 10: 615-624.
Wiley and Pedersen, 1997, "Morphology of moue egg cylinder development in vitro: a light and electron microscopy study", J. Exp. Zoology 200: 389-402.
Campbell et al., 2013, "Epiblast Cell Number and Primary Embryonic Stem Cell Colony Generation are Increased by Culture of Cleavage Stage Embryos in Insulin", J. Reprod. Dev., 59: 131-138.
Rodriguez et al., 2012, "Modulation of Pluripotency in the Porcine Embryo and iPS Cells", PLOS one, vol. 7(11): e49079.
MacGregor et al., "Tissue non-specific alkaline phosphatase is expressed in both embryonic and extraembryonic lineages during mouse embryogenesis but is not required for migration of primordial germ cells", 1995, Dev., 121: 1487-1496.
Niakan and Eggan, "Human pre-implantation embryo development", 2013, Dev. Biol., 375: 54-64.
Pera and Trounson, "Human embryonic stem cells: prospects for development", Development 131, 5515-5525, 2004.
Evans and Kaufman, "Establishment in Culture of Pluripotential Cells from Mouse Embryos", Nature, vol. 292, 1981, pp. 154-156.
Evans, "Origin of mouse embryonal carcinoma cells and the possibility of their direct isolation into tissue culture", J. Reprod. Fert., 62: 625-631, 1981.
Wiley and Pedersen, "Morphology of Mouse Egg Cylinder Development In Vitro: A Light and Electron Microscopic Study", J. Exp. Zool., 200: 389-402, 1977.
Talbot and Garrett, "Ultrastructure of the Embryonic Stem Cells of the 8-Day Pig Blastocyst Before and After In Vitro Manipulation: Development of Junctional Apparatus and the Lethal Effects of PBS Mediated Cell-Cell Dissociation", The Anatomical Record, 264:101-113, 2001.
A. Bradley et al., "Formation of Germ-Line Chimaeras from Embryo-Derived Teratocarcinoma Cell Lines", Nature, vol. 309, May 1984, pp. 255-256.
Brons GM et al. "Derivation of pluripotent epiblast stem cells from mammalian embryos", Nature 2007 448: 191-195.
Hogan B., "From embryo to teratocarcinoma in tissue culture", Nature 1981 292: 111-112.
Hogan B et al., "Manipulating the mouse embryo. A laboratory manual". Second edition. Cold Spring Harbor Laboratory Press, 1994, Section F: Isolation and culture and manipulation of embryonic stem cells, pp. 22-23, 253-288.
P. Hyttel et al., "From Hatching into Fetal Life in the Pig", Acta Scientiae Veterinariae, 2011, 39(Suppl 1), s203-s221.
Martin, G., "Isolation of a pluripotent cell line from early mouse embryos cultured in medium conditioned by teratocarcinoma stem cells", Proc. Natl Acad. Sci. USA, vol. 78, No. 12, pp. 7634-7638, Dec. 1981.
"Teratocarcinomas and embryonic stem cells a practical approach", edited by EJ Robertson IRL Press 1987, Chapter 4, pp. 71-112.
Lee et al., "Establishment and Maintenance of Human Embryonic Stem Cell Lines on Human Feeder Cells Derived from Uterine Endometrium under Serum-Free Condition", Biology of Reproduction, 2005, 72 (1):42-49.
Stringfellow and Siedel, "Manual of the International Transfer Society", Apr. 1998, pp. 106-107.
Talbot et al., "In Vitro Pluripotency of Epiblasts Derived From Bovine Blastocysts", Molecular Reproduction and Development, 42: 35-52, 1995.
Arkell and Tam, "Initiating head development in mouse embryos: integrating signalling and transcriptional activity", Open Biol 2: 120030, 2012.
Hogan B et al., "Manipulating the mouse embryo. A laboratory manual". Second edition. Cold Spring Harbor Laboratory Press, 1994, frontispiece, pp. 56-57.
Tsung et al., "The culture and establishment of embryonic germ (EG) cell lines from Chinese mini swine", Cell Research 13(3), 2003, pp. 195-202.

* cited by examiner

ISOLATING A MAMMALIAN EMBRYONIC STEM CELL FROM A HOMOGENOUS PLURIPOTENT OUTGROWTH OF A MAMMALIAN PRE-IMPLANTATION EMBRYO

This application claims priority from Australian Provisional Patent Application No. 2006905889 filed on 24 Oct. 2006, the contents of which are to be taken as incorporated herein by this reference.

FIELD OF THE INVENTION

The present invention relates to a method of isolating pluripotent cells from embryos, and to pluripotent cells isolated by the method.

BACKGROUND OF THE INVENTION

Embryonic stem (ES) cells are pluripotent cells derived from embryos and which have the ability to differentiate into all three germ layers. In an embryo, such cells contribute to the formation of all tissues and organs of the organism, including the germ cells.

ES cells express a number of specific molecular markers, such as Oct4, Nanog, Sox2, Rex1 and alkaline phosphatase. ES cells also express a number of specific cell surface markers, such as SSEA-1, SSEA-2, TRA 1-60, and TRA 1-81. A further characteristic of undifferentiated ES cells is cytoplasmic organization of F-actin, with associated non-muscle myosin. In undifferentiated ES cells F-actin is organized in periphery organized cortical rings, where cells make direct contact with each other.

The main source of ES cells is the embryoblast, the inner pluripotent component of pre-implantation embryos. In mammals, such as mice and other rodents, primates and humans, this pluripotent component is referred to as the inner cell mass (ICM), because the cells are organised as a clump of pluripotent cells within the early embryo. In ungulates, this component is called the embryonal disk (ED), because the cells of this component are organised as a flattened, mostly one-layered structure.

The research and medical applications of ES cells are well recognised. However, these applications have been hampered by the inability and/or inefficiency of methods of isolation of ES cells from nearly all species.

For example, the efficiency of isolation of ES cells, and the establishment of ES lines, is low. Even for mouse strains that are routinely used to establish ES lines, the efficiency of isolation does not normally exceed 2 to 3% of the embryos used.

The methods of isolating ES cells also generally require a step of separating the pluripotent component from other non-pluripotent cells, such as trophocectoderm and extra-embryonic endoderm, in order to reduce the overgrowth of these other cells. These methods of separating the pluripotent component from other cells usually involve either an immunosurgical step or a step involving the mechanical removal of trophectoderm cells from the inner cell mass.

In this regard, it has also not been possible to isolate pluripotent cells from whole embryos without some form separation of the pluripotent component away from other cells in the embryo.

In addition, for most mammals the establishment of true ES cell lines, in terms of their ability to participate in formation of all organs and tissues (including germline lineages) of chimeric animals, has not yet been reported.

Although there may be a number of reasons for the inability and/or inefficiency for isolating ES cells, it is likely that the small number of cells that are pluripotent in the embryo, and the inability to maintain pluripotent cells isolated from an embryo in an undifferentiated state, contribute to this inability and/or inefficiency.

The present invention relates to a method of isolating pluripotent cells from embryos that does not require separation of the pluripotent component from other cell types and which can also be used to isolate pluripotent cells from whole embryos directly.

A reference herein to a patent document or other matter which is given as prior art is not to be taken as an admission that the document or matter was known or that the information it contains was part of the common general knowledge as at the priority date of any of the claims.

SUMMARY OF THE INVENTION

The present invention provides a method of isolating a pluripotent cell from a pre-implantation embryo including one or more pluripotent cells, the method including:
(i) propagating the one or more pluripotent cells from the embryo under conditions that (a) allow undifferentiated growth of the one or more pluripotent cells and (b) do not allow growth of non-pluripotent cells from the embryo; and
(ii) isolating a pluripotent cell from the one or more pluripotent cells.

The present invention also provides a method of isolating a pluripotent cell from a pre-implantation embryo including one or more pluripotent cells, the method including:
(i) propagating a whole pre-implantation embryo under conditions that (a) allow undifferentiated growth of the one or more pluripotent cells and (b) do not allow growth of non-pluripotent cells from the embryo; and
(ii) isolating a pluripotent cell from the one or more or more pluripotent cells.

The present invention also provides a method of isolating a pluripotent cell from a pre-implantation embryo without isolation of the pluripotent cell from other cells, the method including;
(i) propagating a whole pre-implantation embryo including one or more pluripotent cells under conditions that (a) allow undifferentiated growth of the one or more pluripotent cells and (b) do not allow growth of non-pluripotent cells from the embryo; and
(ii) isolating a pluripotent cell from the one or more pluripotent cells.

The present invention also provides a method of isolating a pluripotent cell from a pre-implantation embryo, the method including propagating one or more pluripotent cells from a pre-implantation embryo in a medium substantially free of serum and isolating a pluripotent cell from the one or more pluripotent cells.

The present invention also provides a method of isolating a pluripotent cell from a pre-implantation embryo, the method including propagating a whole pre-implantation embryo including one or more pluripotent cells in a medium substantially free of serum and isolating a pluripotent cell from the one or more pluripotent cells.

The present invention also provides a method of isolating a pluripotent cell from a pre-implantation embryo without isolation of the pluripotent cell from other cells, the method including propagating a whole pre-implantation embryo including one or more pluripotent cells in a medium substantially free of serum and isolating and isolating a pluripotent cell from the one or more pluripotent cells.

The present invention also provides a method of isolating a pluripotent cell from a pre-implantation embryo, the method including:
(i) establishing a primary culture of cells from the embryo, the primary culture including one or more pluripotent cells;
(ii) propagating the primary culture in a medium that allows undifferentiated growth of the one or more pluripotent cells and does not allow growth of non-pluripotent cells from the embryo; and
(iii) isolating a pluripotent cell from the propagated primary culture.

The present invention also provides a method of isolating a pluripotent cell from a pre-implantation embryo, the method including:
(i) establishing a primary culture of cells from a whole pre-implantation embryo;
(ii) propagating the primary culture in a medium that allows undifferentiated growth of one or more pluripotent cells from the embryo and does not allow growth of non-pluripotent cells from the embryo; and
(iii) isolating a pluripotent cell from the propagated primary culture.

The present invention also provides a method of isolating a pluripotent cell from a pre-implantation embryo, the method including:
(i) establishing a primary culture of cells from the embryo, the primary culture including one or more pluripotent cells;
(ii) propagating the primary culture in a medium that is substantially free of serum; and
(iii) isolating a pluripotent cell from the propagated primary culture.

The present invention also provides a method of isolating a pluripotent cell from a pre-implantation embryo, the method including:
(i) establishing a primary culture of cells from a whole pre-implantation embryo;
(ii) propagating the primary culture in a medium that is substantially free of serum; and
(iii) isolating a pluripotent cell from the propagated primary culture.

The present invention also provides a culture medium when used to propagate one or more pluripotent cells, the medium being substantially free of serum.

The present invention also provides a method of isolating a pluripotent cell from a pre-implantation embryo, the method including:
(i) establishing a primary culture of cells from a whole pre-implantation embryo by depressing the entire embryo into a layer of feeder cells;
(ii) propagating the primary culture in a medium that is substantially free of serum; and
(iii) isolating a pluripotent cell from the propagated primary culture.

The present invention also provides a kit for isolating a pluripotent cell from a pre-implantation embryo, the kit including a medium for propagating one or more pluripotent cells, die medium being substantially free of serum; the kit further optionally including instructions for isolating a pluripotent cell from the embryo.

The present invention also provides a pluripotent cell isolated from a pre-implantation embryo, the pluripotent cell being propagated from one or more pluripotent cells from a whole embryo without isolation of the pluripotent cell from other cells from the embryo.

The present invention also provides a plurality of pluripotent cells isolated from a pre-implantation embryo, the plurality of pluripotent cells being propagated from one or more pluripotent cells from a whole embryo without isolation of the one or more pluripotent cell from other cells from the embryo.

The present invention also provides a pluripotent cell isolated from a pre-implantation embryo, the pluripotent cell being propagated from one or more pluripotent cells from the embryo in a medium substantially free of serum.

The present invention also provides a plurality of pluripotent cells isolated from a pre-implantation embryo, the plurality of pluripotent cells being propagated from one or more pluripotent cells from the embryo in a medium substantially free of serum.

The present invention arises out of studies into the isolation of ES cells from mammalian pre-implantation embryos. In particular, it has been demonstrated that propagating pluripotent cells from an embryo in a medium lacking serum reduces overgrowth of extra-embryonic and other differentiated cells, and also supports the maintenance of the pluripotent cells in an undifferentiated state.

Isolating pluripotent cells in this manner removes the need for artificial isolation of the pluripotent component away from other cells, and also allows pluripotent cells to be isolated from entire embryos. Isolation of pluripotent cells in this manner also removes the need to propagate cells in the presence of a source of serum, which brings with it the potential for contamination with one or more pathogens associated with the serum.

GENERAL DESCRIPTION OF THE INVENTION

Figure 1:
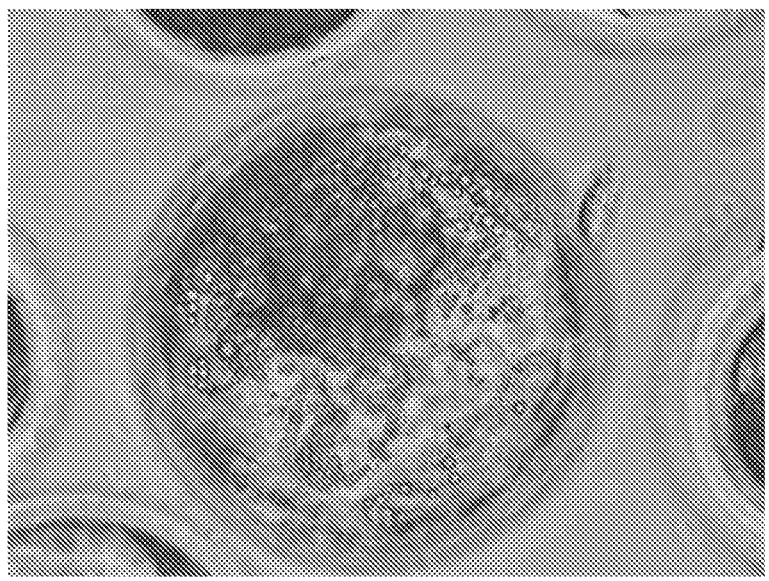
FIG. 1 shows a representative porcine blastocyst used.

As described above, in one embodiment the present invention provides a method of isolating a pluripotent cell from a pre-implantation embryo including one or more pluripotent cells, the method including:
(i) propagating the one or more pluripotent cells from the embryo under conditions that (a) allow undifferentiated growth of the one or more pluripotent cells and (b) do not allow growth of non-pluripotent cells from the embryo; and
(ii) isolating a pluripotent cell from the one or more pluripotent cells.

The present invention is directed to an improved method for isolating pluripotent cells from embryos. The present invention may also be used for the establishment of pluripotent cell lines.

In this regard, the term "pluripotent cell" as used throughout the specification is understood to mean a cell that has one or more of the following characteristics: (i) is able to differentiate into any cell type, including ectoderm, mesoderm, and endoderm derivatives; (ii) is able to contribute to any organs and tissues in a chimeric organism, including the germline lineage; (iii) expresses specific molecular markers (for example Oct4, Nanog, Sox2, Rex 1, alkaline phosphatase) and cell surface markers (for example SSEA-1, SSEA-4, TRA1-60, TRA1-81) indicative of its pluripotent state; and (iv) have characteristic distribution of F-actin in cytoplasm.

The term "one or more pluripotent cells from an embryo" as used throughout the specification is to be understood to mean one or more pluripotent cells of embryonic origin, such as pluripotent cells present in an embryo, or one or more pluripotent cells derived from pluripotent cells originally present in an embryo.

Methods for assessing whether a cell is a pluripotent cell are known in the art.

For example, a pluripotent cell may be identified by morphological characteristics (see for example E. Robertson, "Embryo-derived stem lines." In: *Teratocarcinomas and embryonic stem cells—a practical approach*, ed. E J Robertson, IRL Press, Oxford, 1987, pp 71-112; and Stice S L and Golueke P J, *Cultured inner cell mass cell lines derived from bovine or porcine embryos*, U.S. Pat. No. 5,905,042).

Mouse ES cells for example are typically small, have a large nucleus and minimal cytoplasm, and the nuclei contain one or more prominent dark nucleoli structures, whereas bovine and porcine pluripotent cells exhibit the following properties: a) small cytoplasmic/nuclear volume ratio; b) cytoplasmic vesicles; and c) small individual cells. The expression of certain markers (such as Oct4, Nanog, Sox2, Rex1, alkaline phosphatase, SSEA-1, SSEA-4, TRA 1-60, TRA 1-81) and/or the ability of the cell to differentiate into a variety of cell types, derivatives of ectoderm, mesoderm and endoderm germ layers, are also criteria for the identification pluripotent cells.

Another criterion for identification of ES cells is F-actin distribution. In mouse ES cells F-actin is organized in periphery organized cortical rings, where cells make direct contact with each other. (see for example Slager HG et al. *Organization of non-muscle myosin during early marine embryonic differentiation.* Differentiation. 1992. v. 50. pp. 47-56; Fléchon, J.-E. What are ES Cells? In: *Transgenic animals—Generation and use.* (Houndebine L M-ed.), Harwood Academic Publishers, 1997, pp 157-166).

The term "non-pluripotent cells from an embryo" as used throughout the specification is to be understood to mean those cells of embryonic origin that do not have pluripotent capacity. Such cells include, for example, differentiated cells such as trophoblast cells, cells committed to differentiation, and extra-embryonic endoderm cells. Non-pluripotent cells may be present in the embryo, or be derived from cells originally present in the embryo, such as cells propagated from pluripotent or non-pluripotent cells originally present in an embryo. Methods for characterising cells as pluripotent and non-pluripotent are known in the art.

The embryo may be from a suitable species. Examples of mammalian embryos include an embryo from a human, a primate, a livestock animal including a horse, a cow, a sheep, a pig, or a goat, a companion animal including a dog, a cat, or a laboratory test animal including a mouse, a rat, a guinea pig, or a rabbit.

The pre-implantation embryo in the various embodiments of the present invention may be for example an embryo resulting from fertilization of an oocyte with a sperm, an embryo produced by nuclei transfer, or an embryo produced by parthenogenetic activation. It will be appreciated that the scope of the invention includes isolation of a pluripotent cell from either an in vitro produced embryo or an in vivo produced embryo.

Methods for isolating or producing embryos are known in the art. For example, an embryo may be isolated from a suitable female mammal. Alternatively, the embryo may be produced in vitro, such as by the use of an assisted reproduction technology. An example of a suitable assisted reproduction technology is in vitro fertilization.

The pre-implantation embryo in the various embodiments of the present invention is an embryo that contains one or more pluripotent cells prior to implantation.

The embryo is a suitable pre-implantation embryo, including all suitable embryonic stages from the zygote stage.

In one embodiment, the pre-implantation embryo is a morula or a blastocyst, including an expanded blastocyst or a hatched blastocyst.

In this regard, it will be understood that in the case of an embryo produced by fertilization, the embryo undergoes a series of cleavage divisions after fertilization, progressing through the 2-cell, 4-cell, 8-cell and 16 cell stages. After development of the 8-cell or 16-cell embryo (depending on the species), the blastomeres begin to form tight junctions with one another, leading to deformation of their round shape and formation of a ball-shaped mass of cells, referred to as a morula.

Following formation of junctional complexes between blastomeres, fluid accumulates inside the embryo signalling formation of the blastocyst. The blastocyst is composed of a hollow sphere of trophoblast cells, inside of which is a small cluster of cells, generally referred to as the inner cell mass/embryoblast. The trophoblast goes on to contribute to foetal membrane systems, while a portion of the inner cell mass cells are destined to become the foetus. Generally, the last developmental stage of an embryo before implantation is the hatched blastocyst.

In the human and in other mammals, formation of the blastocyst, including development of cells in the inner cell mass and subsequent differentiation to form the embryonic germ layers and differentiated cells, all follow a similar developmental process.

Typically, a suitable pre-implantation embryo in the various embodiments of the present invention will be selected for the isolation of the pluripotent cell. In this regard, a person skilled in the art will recognise that embryos may have differing development potential, and that embryos that have large and distinct inner cell masses generally provide the most suitable embryos for isolation of pluripotent cells. For example, expanded blastocysts with a large and distinct inner cell mass may be used. Methods for grading embryos are known in the art, for example a blastocyst grading system is described in Veek et al (2003) "Human blastocysts in vitro" Veek L. L. and Zaninovic N., ed. An Atlas of Human Blastocysts. New York pp 99-137; The Parthenon Publishing Group, 2003.

As discussed previously herein, the present invention is directed to an improved method for isolating pluripotent cells from embryos.

In this regard, the term "isolating" will be understood to mean that the pluripotent cell is removed from its natural environment of being present in an embryo.

Thus, the present invention includes the steps of propagating the one or more pluripotent cells from a pre-implantation embryo, and isolating a pluripotent cell from the cells so propagated.

In this regard, it will be understood that the one or more pluripotent cells from the embryo include one or more pluripotent cells present in an embryo, or one or more pluripotent cells originating from pluripotent cells originally present in the embryo. Similarly, non-pluripotent cells from an embryo include non-pluripotent cells present in the embryo or non-pluripotent cells originating from pluripotent or non-pluripotent cells present in the embryo.

In one embodiment, the present invention may be used to enrich one or more pluripotent cells from an embryo in comparison to other non-pluripotent cells.

In another embodiment, the present invention may be used to expand the number of pluripotent cells from the embryo.

For example, the pluripotent cell may be one or more pluripotent cells substantially free of non-pluripotent cells derived from the embryo, such as trophoblast cells, differentiated cells, cells committed to differentiation, and extra-embryonic endoderm cells.

In this regard, trophectoderm cells in particular may hinder the growth of the ICM during the culture period and render the establishment of pluripotent cells and pluripotent cell lines problematic.

In one embodiment, the pluripotent cell so isolated is substantially free of one or more of non-apoptotic non-pluripotent cells derived from the embryo, such as trophoblast cells, differentiated cells, cells committed to differentiation, and extra-embryonic endoderm cells. Methods for determining the apoptotic state of cells are known in the art.

As discussed previously herein, the present invention may also be used for example to establish a pluripotent cell line derived from a pluripotent cell present in an embryo.

In one embodiment, the present invention may be used to obtain a plurality of in vitro pluripotent cells that are substantially free of extra-embryonic cells and/or differentiated cells (including cells committed to differentiate). For example, the present invention may be used to obtain a homogeneous population of pluripotent cells, such as homogeneous colonies of pluripotent cells.

For example, in one embodiment the one or more pluripotent cells of the present invention may be propagated until the cells form a colony of cells.

In one embodiment, the colony so formed may be substantially free of one or more of non-apoptotic non-pluripotent cells, such as trophoblast cells, differentiated cells, cells committed to differentiation, and extra-embryonic endoderm cells.

In one specific embodiment, it has been recognised that the present invention may not only be used to isolate a pluripotent cell from part of an embryo, the present invention may be used to isolate a pluripotent cell from an entire embryo directly.

Thus, the propagation of the one or more pluripotent cells in the various embodiments of the present invention may be propagation of a whole embryo containing the one or more pluripotent cells.

Accordingly, in another embodiment the present invention provides a method of isolating a pluripotent cell from a pre-implantation embryo including one or more pluripotent cells, the method including:

(i) propagating a whole pre-implantation embryo under conditions that (a) allow undifferentiated growth of the one or more pluripotent cells and (b) do not allow growth of non-pluripotent cells from the embryo; and
(ii) isolating a pluripotent cell from the one or more or more pluripotent cells.

As discussed above, the present invention may also be used to isolate a pluripotent cell from a pre-implantation embryo without employing one or more steps to isolate the pluripotent cell away from other cells, such as trophectoderm cells.

Accordingly, in one embodiment the present invention provides a method of isolating a pluripotent cell from a pre-implantation embryo without isolation of the pluripotent cell from other cells, the method including:
  (i) propagating a pre-implantation embryo including one or more pluripotent cells under conditions that (a) allow undifferentiated growth of the one or more pluripotent cells and (b) do not allow growth of non-pluripotent cells from the embryo; and
  (ii) isolating a pluripotent cell from the one or more or more pluripotent cells.

As discussed above, in one embodiment the embryo is a whole embryo.

Thus, the present invention may also be used to isolate a pluripotent cell from a whole embryo without isolation of the pluripotent cell from other cells.

Accordingly, in another embodiment the present invention provides a method of isolating a pluripotent cell from a whole pre-implantation embryo without isolation of the pluripotent cell from other cells, the method including:
  (i) propagating a whole pre-implantation embryo including one or more pluripotent cells under conditions that (a) allow undifferentiated growth of the one or more pluripotent cells and (b) do not allow growth of non-pluripotent cells from the embryo; and
  (ii) isolating a pluripotent cell from the one or more or more pluripotent cells.

Examples of such methods used to isolate pluripotent cells from other cells (such as trophoblast cells) include mechanical, immunosurgical, non-enzymatic or enzymatic methods of isolation.

The present invention also provides pluripotent cells isolated according to the present invention. The present invention also provides a multiponent or differentiated cell derived from the pluripotent cell. Methods for differentiating pluripotent cells along specific developmental lineages, and characterising the cells, are known in the art.

Accordingly, in another embodiment the present invention provides a pluripotent cell isolated from a pre-implantation embryo, the pluripotent cell being propagated from one or more pluripotent cells from a whole embryo without isolation of the pluripotent cell from other cells from the embryo.

The present invention also provides a plurality of pluripotent cells, such as a homogenous population of cells. For example, the population of cells may be a colony of pluripotent cells.

Accordingly, in another embodiment the present invention provides a plurality of pluripotent cells isolated from a pre-implantation embryo, the plurality of pluripotent cells being propagated from one or more pluripotent cells from a whole embryo without isolation of the pluripotent cell from other cells from the embryo.

As discussed previously herein, the propagation of the one or more pluripotent cells in the various embodiments of the present invention is propagation of the cells under conditions that allow undifferentiated growth of pluripotent cells and do not allow growth of non-pluripotent cells from the embryo. Methods for determining whether culture conditions meet these criteria are known in the art.

In one embodiment, the propagation of the one or more pluripotent cells is propagation substantially in the absence of serum.

In one embodiment, the one or more pluripotent cells from the embryo are propagated in a culture medium that is substantially free of serum.

Thus, the present invention includes propagating the cells in a suitable medium that is substantially free of serum, such as a medium that does not contain serum.

Accordingly, in another embodiment the present invention provides a method of isolating a pluripotent cell from a pre-implantation embryo, the method including propagating one or more pluripotent cells from the embryo in a medium substantially free of serum.

In this regard, it has been recognised that the presence of serum in the culture medium may contribute to the low efficiency of isolation and maintenance of pluripotent cells. Without being bound by theory, it is believed that the presence of serum in a culture medium is not only responsible for overgrowth of extra-embryonic cells, but also for promoting differentiation of pluripotent cells. Thus, serum may not only provide nutrients for growing cells, but it may also contain undefined factors which can promote differentiation of pluripotent cells and/or support differentiation of cells.

Accordingly, the propagation of the pluripotent cells from the embryo in this manner allows elimination of extra-embryonic cells (such as trophectoderm and extra-embryonic endoderm) and the elimination of cells that have differentiated and/or committed to differentiation.

In one embodiment, the zona pellucida of the embryo is removed before propagation of the one or more pluripotent cells. For example, the zona pellucida may be removed by enzymatic or mechanical removal. Methods for removing the zona pellucida of mammalian embryos are known in the art.

The present invention also provides a pluripotent cell or a plurality of cells isolated by this method.

Accordingly, in another embodiment the present invention provides a pluripotent cell isolated from a pre-implantation embryo, the pluripotent cell being propagated from one or more pluripotent cells from the embryo in a medium substantially free of serum.

In another embodiment, the present invention provides a plurality of pluripotent cells isolated from a pre-implantation embryo, the plurality of pluripotent cells being propagated from one or more pluripotent cells from the embryo in a medium substantially free of serum.

In this regard, a substantially serum free medium is a medium that is free of serum or a medium that includes a level of serum protein(s) or other components that still allows elimination of extra-embryonic cells and the elimination of cells that have differentiated and/or committed to differentiation.

In one embodiment, the medium is serum free.

In this regard, it will be appreciated that as serum is a mixture of various components, a medium that is substantially free of serum may still contain one or more components normally found in serum, but which do not promote differentiation and growth of non-pluripotent cells.

Methods for determining the ability of specific factors to promote differentiation and growth of non-pluripotent cells are known in the art.

In one embodiment, the propagation of the one or more pluripotent cells is in a medium that includes a serum replacement. A suitable serum replacement is available for example from Invitrogen (Cat. No. 10828-028), or a serum replacement such as Ultroser G (Pall). Serum replacement is defined serum substitution, containing highly purified animal (generally bovine) proteins such as serum albumin, insulin and transferrin. Serum replacement does not usually, but may, contain growth factors, steroid hormones, glucocorticoids and cell adhesion factors.

A suitable concentration of serum replacement is in the range from 5 to 25%.

In another embodiment, the propagation of the one or more pluripotent cells is in a medium that includes albumin.

A suitable of concentration of albumin is in the range from 0.1 to 10%.

A suitable medium for the propagation of the one or more pluripotent cells from the embryo is α-MEM medium (Invitrogen, Cat. No 32571-036) containing GlutaMax-I (dipeptide L-alanyl-L-Glutamime), substituted on a molar equivalent basis for L-glutamine, ribonucleosides and deoxyribonucleosides, and supplemented with 0.1 mM-10 mM sodium pyruvate, 1-100 ng/mL bFGF, 1-100 ng/mL hrEGF, 1X ITS, 55 uM β-mercaptoethanol, 1× non-essential amino acids (all from Invitrogen) and 1-100 ng/mL hrLIF (Millipore).

In this regard, culture conditions are known in the art for embryos from a wide variety of species, for example as described in E. Robertson, "Embryo-derived stem lines." In: *Teratocarcinomas and embryonic stem cells—a practical approach*, ed. E J Robertson, IRL Press, Oxford, 1987, pp 71-112.

Suitable base media include for example DMEM medium, DMEM/F12 medium, alpha-MEM medium and HEScGRO medium. Other suitable base media may be determined by a person skilled in the art.

In one embodiment, the pre-implantation embryo is a whole embryo.

Accordingly, in another embodiment the present invention provides a method of isolating a pluripotent cell from a pre-implantation embryo, the method including propagating a whole pre-implantation embryo including one or more pluripotent cells in a medium substantially free of serum.

The present invention also provides a culture medium when used to propagate one or more pluripotent cells, the medium being substantially free of serum. In one embodiment, the medium includes a serum replacement.

Suitable culture media are as previously described herein.

The present invention also provides a kit for isolating a pluripotent cell from a pre-implantation embryo. The kit includes a medium substantially free of serum for propagating the embryo and may further include instructions for isolating a pluripotent cell.

Accordingly, in another embodiment the present invention provides a kit for isolating a pluripotent cell from a pre-implantation embryo, the kit including a medium for propagating one or more pluripotent cells, the medium being substantially free of serum; the kit further optionally including instructions for isolating a pluripotent cell from the embryo.

In one embodiment, the medium in the kit also includes a serum replacement.

Alternatively, the kit also contains separately a serum replacement, which is added to the medium for use.

In one embodiment, the propagating of the one or more pluripotent cells includes establishing a primary culture of cells from all or part of the embryo, the embryo containing one or more pluripotent cells.

Accordingly, in another embodiment the present invention provides a method of isolating a pluripotent cell from a pre-implantation embryo, the method including:
(i) establishing a primary culture of cells from the embryo, the primary culture including one or more pluripotent cells;
(ii) propagating the primary culture in a medium that allows undifferentiated growth of the one or more pluripotent cells and does not allow growth of non-pluripotent cells from the embryo; and
(iii) isolating a pluripotent cell from the propagated primary culture.

In one embodiment, the primary culture is established by propagating all or part of the embryo in the presence of feeder cells.

In this case, all or part of the embryo may be for example depressed, embedded or flattened into a layer of feeder cells.

Generally, the feeder layer will be an inactivated feeder later, treated so as to inhibit proliferation of the feeder cells. Methods of treating the feeder layer to inhibit proliferation include irradiation (eg γ-irradiation) or treatment with chemical agents, such as mitomycin C. Suitable cells for use as a feeder layer include cells such as mouse embryonic fibroblasts. Methods for preparing a suitable feeder layer are known in the art.

In one embodiment, the primary culture is established by propagating a whole embryo directly in the presence of feeder cells.

Accordingly, in another embodiment the present invention provides a method of isolating a pluripotent cell from a pre-implantation embryo, the method including:
(i) establishing a primary culture of cells from a whole pre-implantation embryo;
(ii) propagating the primary culture in a medium that allows undifferentiated growth of one or more pluripotent cells from the embryo and does not allow growth of non-pluripotent cells from the embryo; and
(iii) isolating a pluripotent cell from the propagated primary culture.

Alternatively, the primary culture may be established by propagating all or part of the embryo on a suitable cell growth substrate.

As discussed previously herein, in one embodiment the propagation of the primary culture is in a medium that is substantially free of serum.

Accordingly, in another embodiment the present invention provides a method of isolating a pluripotent cell from a pre-implantation embryo, the method including:
(i) establishing a primary culture of cells from the embryo, the primary culture including one or more pluripotent cells;
(ii) propagating the primary culture in a medium that is substantially free of serum; and
(iii) isolating a pluripotent cell from the propagated primary culture.

In one embodiment, a primary culture is established directly from a whole pre-implantation embryo.

Accordingly, in another embodiment the present invention provides a method of isolating a pluripotent cell from a pre-implantation embryo, the method including:
(i) establishing a primary culture of cells from a whole pre-implantation embryo;
(ii) propagating the primary culture in a medium that is substantially free of serum; and
(iii) isolating a pluripotent cell from the propagated primary culture.

In one embodiment, the zona pellucida of the embryo is removed before propagation of the one or more pluripotent cells. For example, the zona pellucida may be removed by enzymatic or mechanical removal. Methods for removing the zona pellucida of mammalian embryos are known in the art.

As described previously herein, the primary culture may be established by depressing all or part of the embryo into the feeder layer.

Accordingly, in another embodiment the present invention provides a method of isolating a pluripotent cell from a pre-implantation embryo, the method including:
(i) establishing a primary culture of cells from a whole pre-implantation embryo by depressing the entire embryo into a layer of feeder cells;
(ii) propagating the primary culture in a medium that is substantially free of serum; and
(iii) isolating a pluripotent cell from the propagated primary culture.

The propagation of the primary culture may be for a suitable time to allow proliferation or maintenance of the one or more pluripotent cells, depending upon for example the enrichment and/or expansion of cells required.

In one embodiment, the zona pellucida of the embryo is removed before propagation of the one or more pluripotent cells. For example, the zona pellucida may be removed by enzymatic or mechanical removal. Methods for removing the zona pellucida of mammalian embryos are known in the art.

For example, the primary culture may be cultured for a period of 7 to 14 days to allow production of a homogenous population of pluripotent cells substantially free of extra-embryonic cells or containing a small amount of apoptotic extra-embryonic cells, such as trophectoderm cells.

In one embodiment, the primary culture is cultured for a period of time sufficient to allow the formation of colonies of homogenous pluripotent cells. Thus, the colony may be substantially free of non-pluripotent cells, such as trophectoderm cells and other differentiated cells, cells committed to differentiate and extra-embryonic endoderm cells.

The pluripotent cells so isolated may be passaged multiple times without any loss of morphological criteria of undifferentiated cells and pluripotency.

The present invention also provides a pluripotent cell, or a pluripotent cell line, produced according to the present invention.

The present invention also provides cells of further restricted potency (eg multipotent cells) or differentiated cells derived from the pluripotent cells produced according to the present invention, and genetically manipulated cells derived from the pluripotent cells. Methods for differentiating pluripotent cells and for genetic manipulation are known in the art.

The present invention also provides a non-human animal including one or more cells derived from the pluripotent cell produced according to the present invention. Methods for producing such animals are known in the art.

For example, the animal may contain a number of cells derived from a pluripotent cell produced according to the present invention, such as a chimeric animal.

The present invention also provides a composition including one or more pluripotent cells produced according to the present invention. The composition may be used in vitro or in vivo.

In this regard, the present invention also contemplates the use of the pluripotent cells produced according to the present invention (and differentiated and genetically manipulated forms thereof), to regenerate cells in a tissue or in a subject, by introducing the cells into the tissue or subject.

Thus, in another embodiment the present invention contemplates a pharmaceutical composition including cells produced according to the present invention, and/or a pharmaceutical composition including differentiated cells derived from the pluripotent cells and/or genetically manipulated cells derived from the pluripotent cells.

Methods for formulating pharmaceutical composition for cell therapy are known in the art, for example as described in "Stem Cell Transplantation—Biology, Processing and Therapy" (2006) ed. By Anthony D. H. Ronald-Hoffman and Esmail P. Zanjani, Wiley-VCH Verlag GmbH & co kGaA; "Cell Therapy, Stem Cells and Brain Therapy" (2006) ed. By Paul R. Sunberg and Cyndy D. Davis, Humana Press.

Generally, such pharmaceutical compositions include the cells and a pharmaceutically acceptable carrier.

The need for cell therapy to regenerate cells in a target tissue may be associated with a number of diseases or conditions associated with cell loss, damage or dysfunction.

Accordingly, the present invention may also be used to prevent and/or treat a disease or condition in a subject associated with cell loss, cell damage or cell dysfunction, the method including the step of introducing cells according to the present invention into a subject.

The subject may be any suitable recipient, including a mammal as previously discussed herein. Methods for introducing cells into recipient mammals and humans are known in the art.

Description of Specific Embodiments

Reference will now be made to experiments that embody the above general principles of the present invention. However, it is to be understood that the following description is not to limit the generality of the above description.

EXAMPLE 1

In vitro Production of Porcine Blastocysts

Porcine ovaries were obtained from a local slaughterhouse. Oocytes were aspirated and matured in TCM-199 medium in a humidified atmosphere of 5% carbon dioxide at 39° C. After 42-44 hours of maturation, oocytes were fertilized for 6 hours in TALP-PVA medium with boar sperm, used at a concentration $5 \times 10^6$ spermatozoa/mL. After fertilization, fertilized oocytes were cultured in NCSU-23 medium for 7 days. Day of fertilization is day 0. Hatched or expanded blastocysts developed at day 7 of in vitro culture (FIG. 1) were used for the isolation of putative pluripotent porcine ES cells.

EXAMPLE 2

In vivo Production of Porcine Blastocysts

Sows in heat were artificially inseminated with boar semen. At day 4.5 after insemination fresh, in vivo produced embryos, were flushed out of uterine horns at late morulae-early blastocyst stage and cultured overnight in NCSU-23 medium as described in Example 1. Expanded blastocysts developed at day 6 after artificial insemination were used for the isolation of putative pluripotent ES cells.

EXAMPLE 3

Preparation of Feeder Layers from Primary Mouse Embryonic Fibroblasts

Methods for the preparation of feeder layers from primary mouse embryonic fibroblasts are as described in E. Robertson, "Embryo-derived stem lines." In: *Teratocarcinomas and embryonic stem cells—a practical approach*, ed. E J Robertson, IRL Press, Oxford, 1987, pp 71-112. Briefly, 129/Sv pregnant female mice were sacrificed on the fourteenth day of pregnancy. Fetuses were removed and the liver, heart and other visceral organs discarded. The remaining fetuses were fine minced in presence of trypsin and EDTA and incubated for 10-15 min at 37° C. Trypsin was then neutralized and cells plated onto Falcon tissue flasks and incubated at 37° C. in humidified atmosphere 5% carbon dioxide until the cells were confluent. When cells reached confluency, they were harvested by trypsinization, the trypsin inactivated and the cells frozen in cryotubes in 10% DMSO in serum at a concentration $2\text{-}5\times10^6$ cell/mL/tube and stored under −80° C. For preparation of feeder layers, the tubes were thawed, cells washed to remove DMSO and grown in culture flasks until confluence. Upon confluence, cells were trypsinized, trypsin inactivated, and washed cells gamma-irradiated and plated at $1.2\text{-}1.5\times10^5$ cells/cm$^2$ into Falcon organ culture dishes for two days before use.

EXAMPLE 4

Depression of Zona Pellucida Free Porcine Blastocysts into Feeder Layers.

Figure 2:
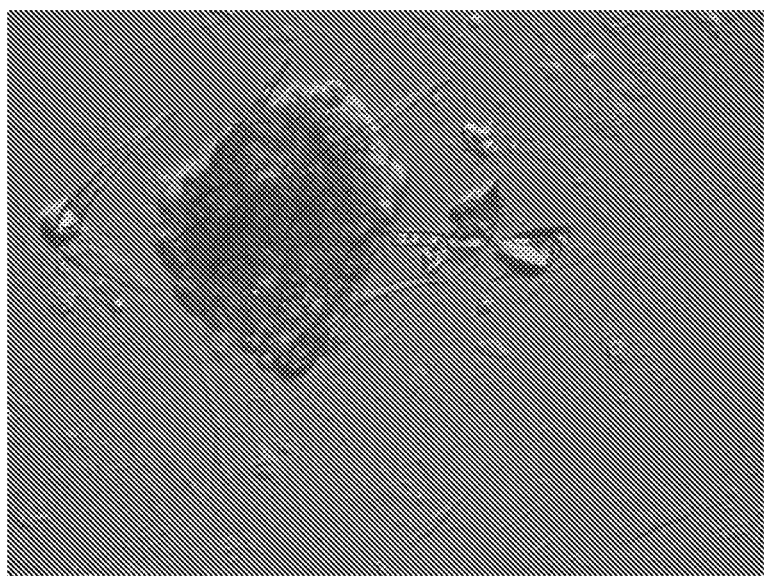
FIG. 2 shows a blastocyst after removal of the zona pellucida and depression into mouse embryonic fibroblast (MEF) feeder layer.
Figure 3A:
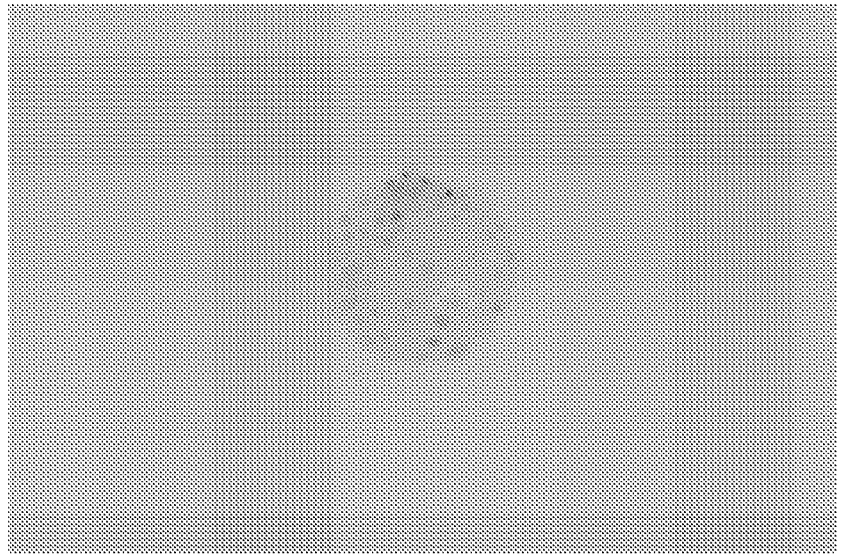
FIG. 3 shows cell numbers in a porcine blastocyst prior (Panel A) and after (Panel B) its depression into feeder layer. It should be noted that the cell numbers have been not reduced after depression of the whole blastocyst into feeder layer, and that the depression into the feeder layer has not resulted in mechanical separation of embryonal disk and trophoblast cells.
Figure 3B:
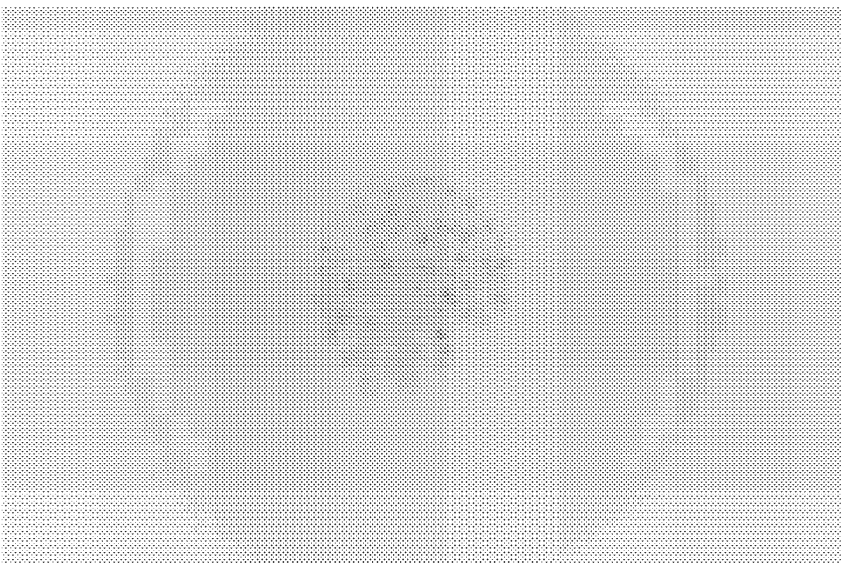

Porcine hatched or expanded blastocysts were obtained as described in Example 1 and Example 2. A representative blastocyst is shown in FIG. 1. To mechanically remove the zona pellucida from expanded blastocysts, they were carefully pipetted with a mouth-controlled glass pipette with an inner diameter of tip slightly less then the diameter of the blastocysts. After two-three rounds of pipetting, zona pellucida were easily removed without damage of the blastocyst. Zona pellucida free porcine embryos were then transferred into Falcon organ culture dishes containing a feeder layer and carefully depressed into feeder layer using insulin syringes with 30 G needles. The depression of embryos into feeder layers does not result in cell loss or mechanical separation of pluripotent cells from trophoblast cells. This is shown in FIGS. 2 and 3. Embryos were stained with vital DNA stain Hoechst 33342 at a concentration of 50 nM and cell numbers counted before and after depression. The results from this study (shown in FIGS. 3A and 3B) demonstrated that neither cell loss or separation of pluripotent and non-pluripotent components of embryo were occurred during the depression procedure.

EXAMPLE 5

Isolation of Pluripotent Cells

Porcine day 6-day 7 hatched or expanded blastocysts were obtained as described in Example 1 and Example 2. A representative blastocyst is shown in FIG. 1.

After removal of the zona pellucida, the embryo was depressed into a mouse embryonic fibroblast feeder layer, as described in Example 3 and shown in FIG. 2, and cultured for 12-15 days in alpha-MEM medium (Invitrogen, Cat No 32571-036) containing Glutamax-I (dipeptide L-alanyl-L-glutamine), substituted on molar equivalent basis for L-glutamine, ribonucleosides and deoxyribonucleosides, and supplemented with 1 mM sodium pyruvate, 10 ng/ml bFGF, 10 ng/ml hrEGF, 1X ITS, 55 um beta-mercaptoethanol, 1× non-essential amino acids (all from Invitrogen) and 10 ng/ml hrLIF (Millipore).

To culture medium 20% of Hyclone ES screened FCS (control FCS group) or 10% of Invitrogen SR (experimental SR group) were added.

Development of the embryo depressed into the feeder layer in each group was monitored on a daily basis, with the medium for each group being changed every 3 days.

Figure 4:
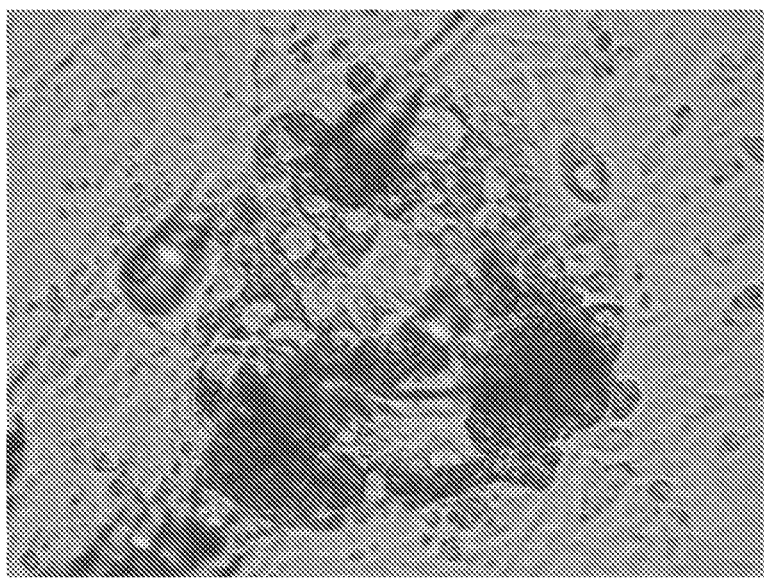
FIG. 4 shows formation of primary embryonal outgrowth in control (FCS) group and experimental (serum replacement, SR) group. In both groups embryonal outgrowths consisted of trophectoderm cells and putative ES cells.

On the second day of culture, depressed embryos in both groups formed embryonal outgrowths consisting of trophectoderm cells and putative ES cells (FIG. 4).

Further culture of embryonal outgrowths for an extended period of time resulted in development morphologically distinguishable structures in the control (FCS group) and experimental groups (SR group).

Figure 5:
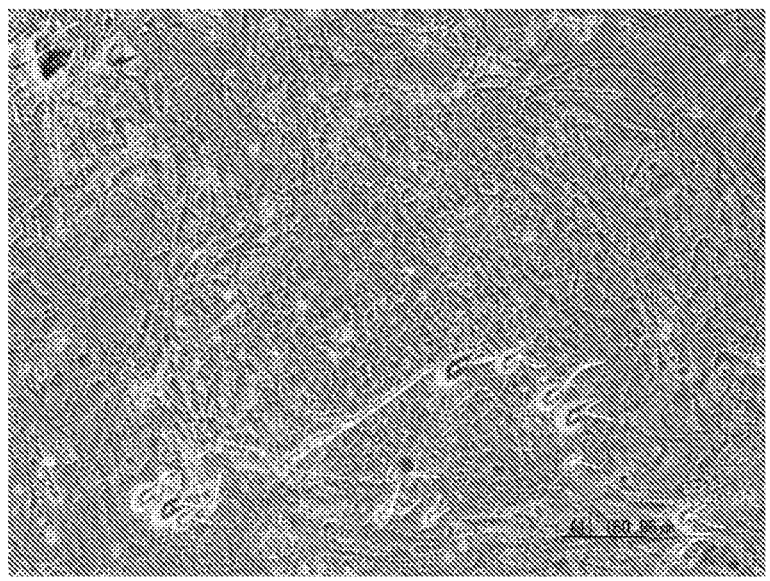
FIG. 5 shows development of primary embryonal outgrowth in FCS group after 7 days in culture. Embryonal outgrowth consists of differentiated cells without any signs of presence of putative ES cells.
Figure 6:
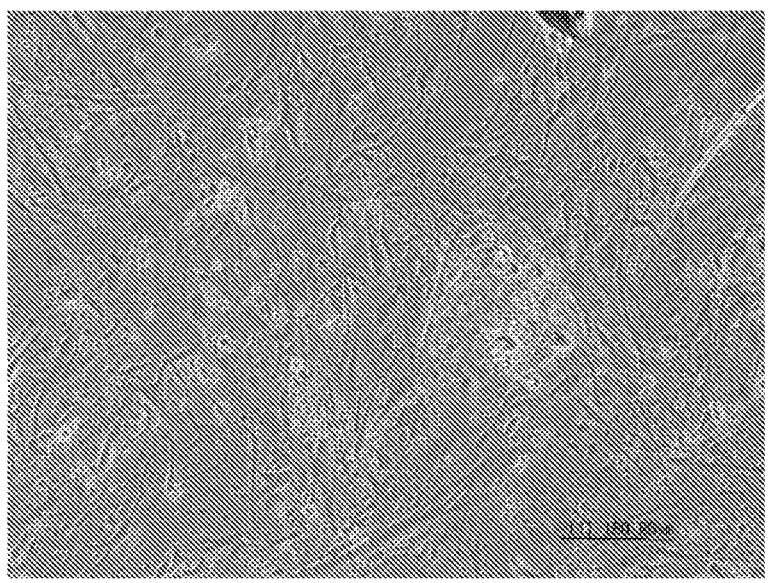
FIG. 6 shows development of primary embryonal outgrowth in FCS group after 7 days in culture. In this embryonal outgrowth, the small colony of putative ES cells is surrounded with differentiated cells.

After culturing for 7 days, embryonal outgrowths of the FCS group consisted of differentiated cells (FIG. 5) or very small putative ES cell component surrounded with differentiated cells (FIG. 6). In the best case in this group, primary embryonal outgrowth formation after 2 weeks in culture resulted in formation of colonies consisting of hardly passageable (less than 0.5 mm in diameter) PC surround with differentiated cells.

Figure 7:
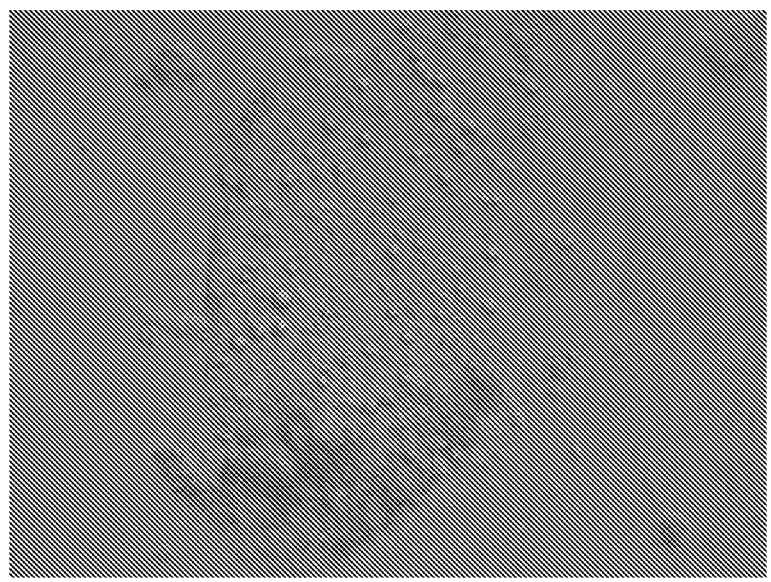
FIG. 7 shows primary embryonal outgrowth in SR group after 7 days in culture. The embryonal outgrowth consists of putative porcine ES cells with morphology characteristic of ES cells (small cytoplasmic/nuclear ratio, nuclei with multiple nucleoli, and multiple lipid inclusions in cytoplasm) with a small amount of apoptotic trophectoderm cells.
Figure 8:
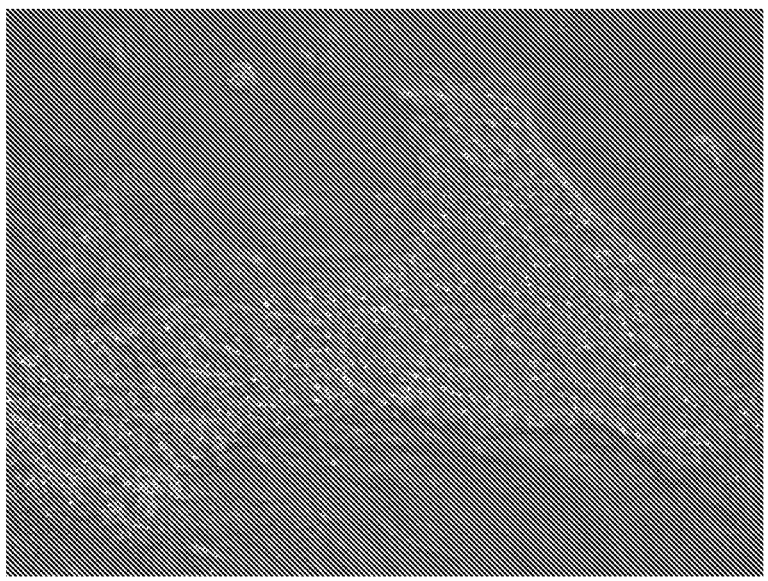
FIG. 8 shows primary embryonal outgrowth in SR group after 7 days in culture. The outgrowths consist of only homogenous putative porcine ES cells with characteristic morphology.

In the SR group, after 7 days in culture the embryonal outgrowths consisted of putative porcine ES cells with morphology characteristic for ES cells (small cytoplasmic/nuclear ratio, nuclei with multiple nucleoli, and multiple lipid inclusions in cytoplasm) with a tiny amount of apoptotic trophectoderm cells (FIG. 7) or embryonal outgrowths consisting of only homogeneous putative porcine ES cells with characteristic morphology (FIG. 8).

Figure 9:
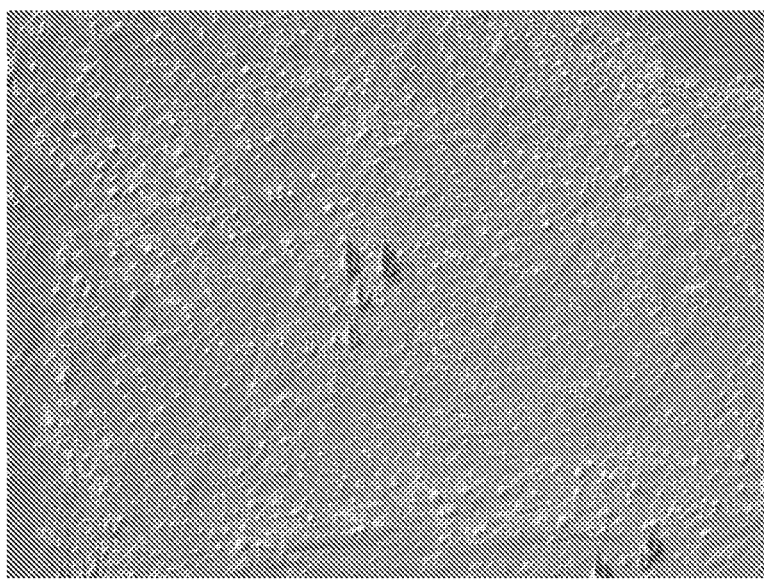
FIG. 9 shows primary embryonal outgrowth in SR group after 14 days in culture. Primary embryonal outgrowth is significantly expanded and consists of homogeneous putative ES colonies without any signs of trophectoderm or other differentiated cells

Further cultivation of the SR embryonal outgrowths in the next 7 days resulted in formation of homogenous putative ES cell line colonies without any signs of trophectoderm or other differentiated cells (FIG. 9).

These porcine ES cell line colonies are easily mechanically passageable, since at that time they had reached about 3 mm in diameter. Porcine ES cell lines, produced with the above described method described could be stored in liquid nitrogen in a frozen state as a chunk or mass of colonies with survival rate close to 95% after thawing. Frozen-thawed porcine ES colonies grown under conditions described herein have the same criteria of undifferentiated state as founder colonies. These porcine ES cell lines could be maintained in culture for multiple passages without any loss of morphological criteria or undifferentiated cells and pluripotency.

EXAMPLE 6

Oct 4 Expression in Day 2 Primary Outgrowth of Porcine Blastocysts.

Figure 10A:
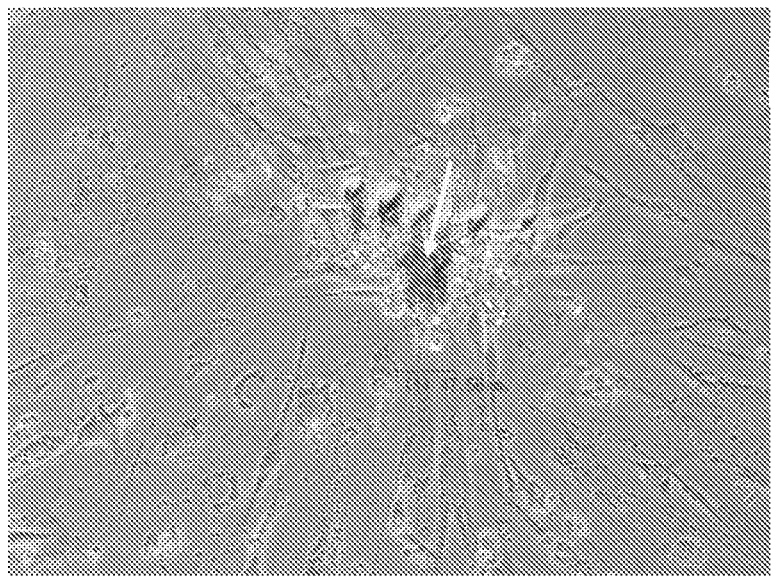
FIG. 10 shows expression of OCT-4 in primary 2 days old primary outgrowth, consisting (Panel A) rest of trophoblast cells and cells, identified as pluripotent cells (yellow arrow). Panel B shows, that only pluripotent cells (yellow arrow) express Oct-4 (green).
Figure 10B:

Porcine day 6-day 7 hatched or expanded blastocysts were obtained as described in Example 1 and Example 2, and plated onto a feeder layer as described in Example 5. After 2 days in culture embryonal outgrowths were fixed in 4% paraformaldehyde and stained with primary goat anti-Oct-4 polyclonal (IgG) antibodies. Secondary antibodies were donkey anti-goat IgG antibodies, labeled with FITC. Samples were analyzed under epi-fluorescent microscope. As shown in FIG. 10A, porcine embryonal outgrowth consisted of group of cells, identified by morphology as putative ES cells (yellow arrow) and rests of trophoblast cells. As shown in FIG. 10B, only cells, identified by morphology as putative ES cells, expressed Oct-4 (yellow arrow).

EXAMPLE 7

Cytoplasm/Nucleus Ratio in Porcine ES Cells.

Figure 11A:
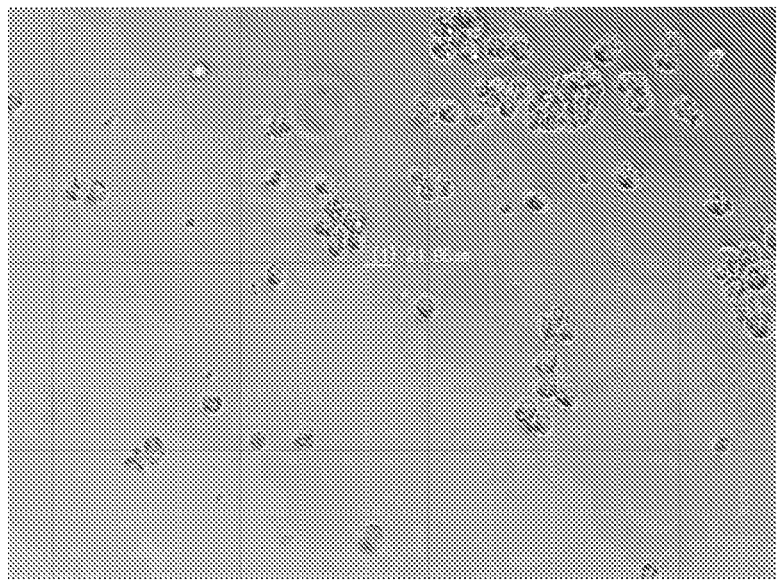
FIG. 11 shows high cytoplasm/nucleus ration in single porcine ES cells. These cells are small in diameter (Panel A) and have lipid inclusions in their cytoplasm. Nuclei in these cells (Panel B; nuclei are stained in red) take almost whole volume of cells.
Figure 11B:
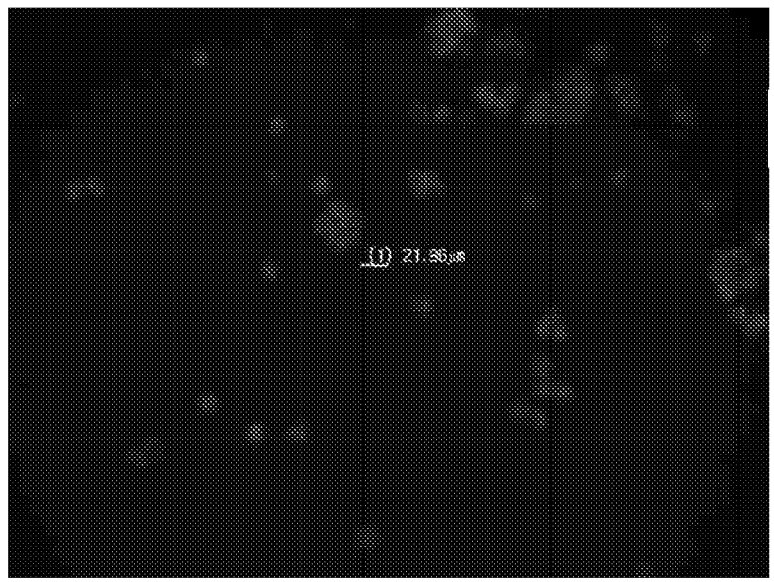

Porcine embryonic stem cells (ES cells) were isolated as described in Example 5. After several passages in vitro, porcine ES cells were enzymatically dissociated with TrypLE Express (Invitrogen) to produce single cell suspension of porcine ES cells. The nuclei of produced single cells were stained with Cyto-64 Red Fluorescent Nucleic Acid Stain (Invitrogen) at concentration 50 nM. As shown in FIG. 11A, porcine ES cells are small size cells with approximately 11-13 μm in diameter. As shown in FIG. 11B, the nuclei of porcine ES cells occupy almost the whole volume of the cells, ie these cell have low cytoplasm/nucleus ratio (or high nucleus/cytoplasm ratio), characteristic for ES cells.

EXAMPLE 8

High Affinity of Porcine ES Cells to ICM Cells of Porcine Blastocysts

Figure 12A:
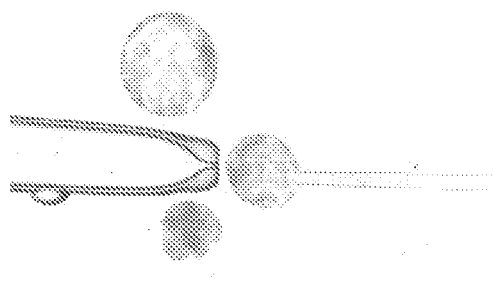
FIG. 12 shows results of injection of porcine ES cells into porcine blastocysts. Set of single porcine ES cells labelled with red fluorescent stain (Panel A and Panel B) were injected into host porcine blastocysts. Next day after injection, host blastocysts restored their shape (Panel C), and injected porcine ES cells were able to integrate into ICM of blastocysts (Panel D).
Figure 12B:
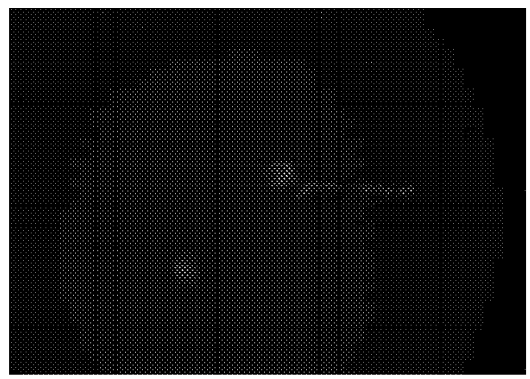
Figure 12C:
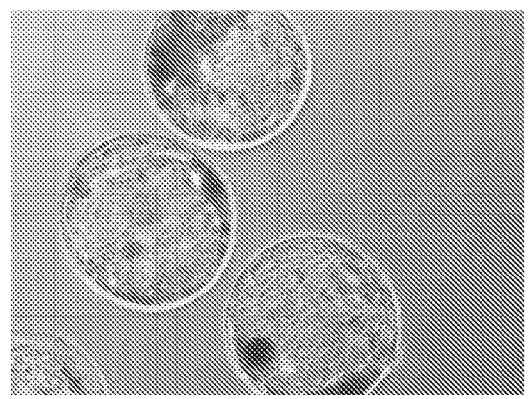
Figure 12D:

As shown at FIGS. 12A and 12B, porcine ES cells after several passages, prepared as single cell suspension and stained with Cyto 64 (as described in Example 7) were injected into Day 5 in vitro produced recipient porcine blastocysts. Recipient porcine blastocysts were produced as described in Example 1. After injection, blastocysts were cultured overnight in culture medium described in Example 1. Just after injection blastocysts were collapsed (FIGS. 12A and 12B), but restored their shape (FIG. 12C) after overnight culture. As shown in FIG. 12D, injected porcine ES cell were able to integrate into ICM of recipient blastocysts, demonstrating, thereby, high affinity of porcine ES cells to ICM cells of porcine blastocysts.

EXAMPLE 9

F-Actin Pattern in Porcine Trophoblast Cells and Porcine ES Cells.

Figure 13A:
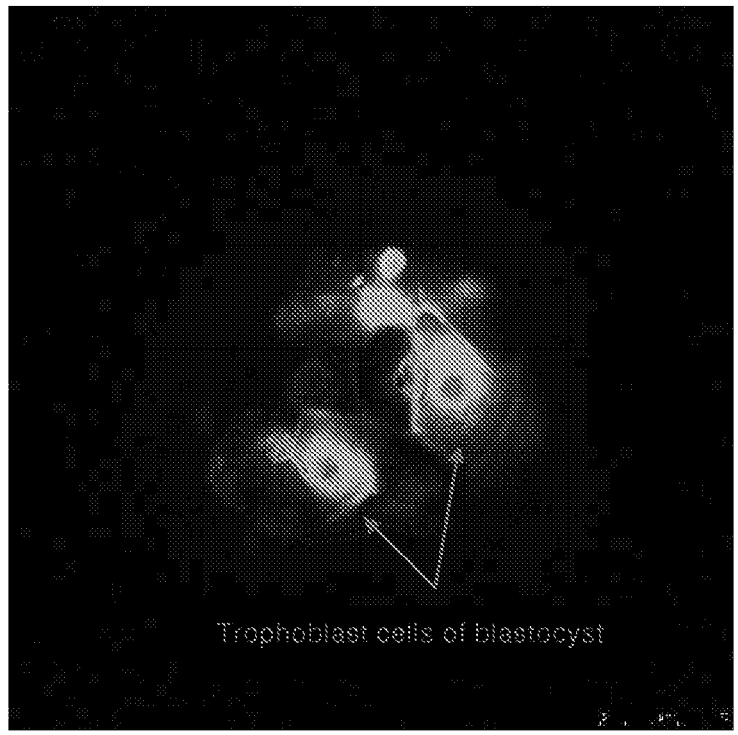
FIG. 13 shows F-actin organization (green) in porcine trophoblast cells (Panel A) mouse embryonic fibroblast cells and porcine ES cells (Panel B). Porcine ES cells have F-actin distribution pattern characteristic for ES cells.
Figure 13B:
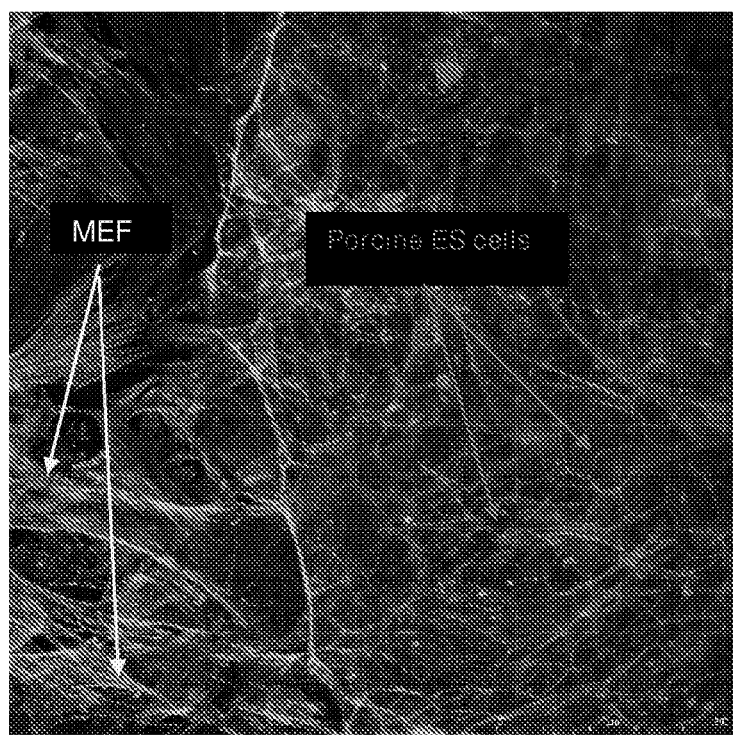

Porcine Day 7 in vitro blastocysts were produced as described in Example 1. Porcine ES cells were isolated and maintained in culture for several passages as described in Example 5. Porcine blastocysts and colonies of porcine ES cells were fixed in 4% paraformaldehyde and stained with phalloidin (bicyclic heptapeptide, binds to F-actin filaments) labelled with Alexa Fluor 488 (Invitrogen). As shown at FIG. 13A, trophoblast cells (red arrows), the first differentiated cells in porcine embryos, have diffused distribution of F-actin (green) through whole cytoplasm. As shown at FIG. 13B, mouse embryonic fibroblasts contain extensive F-actin (green) microfilament bundles (yellow arrows) through out the cytoplasm, whereas F-actin (green) in cells of porcine ES colonies are organized on periphery of cells (red arrows), where cells have direct contact with each other This pattern of F-actin organization is characteristic for ES cells.

EXAMPLE 10

SSEA-1 Expression in Porcine ES Cells

Figure 14:
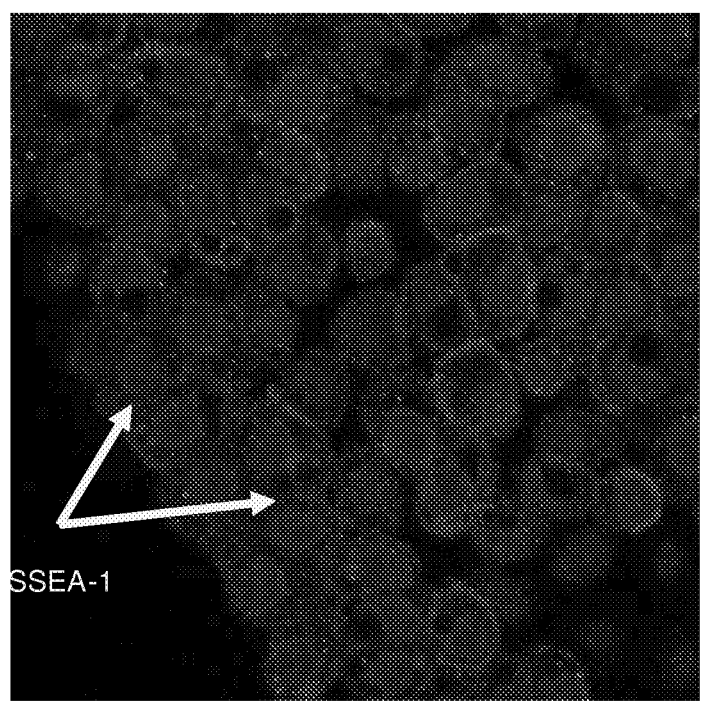
FIG. 14 shows SSEA-1 expression (red) in porcine ES cells.

Porcine ES cells, isolated and maintained in culture for several passages as described in Example 5, were fixed with 4% paraformaldehyde and stained with primary mouse anti-SSEA-1 antibodies (IgM). Secondary antibodies were goat anti-mouse (IgM) antibodies labeled with rhodamine. After staining porcine ES cell colonies were embedded into SlowFade antifage reagent with DAPI (Invitrogen). As shown in FIG. 14, porcine ES cells intensively express SSEA-1 (red), a marker of pluripotency.

EXAMPLE 11

Oct-4 Expression in Porcine ES Cells

Figure 15:
FIG. 15 shows Oct-4 expression (green) in porcine ES cells.

Porcine ES cells, isolated and maintained in culture for several passages as described in Example 5, were fixed with 4% paraformaldehyde and stained with primary goat anti-Oct-4 polyclonal (IgG) antibodies. Secondary antibodies were donkey anti-goat IgG antibodies, labeled with FITC. Samples were analyzed under epi-fluorescent microscope. As shown in FIG. 15, porcine ES cells express Oct-4, a marker of pluripotency.

EXAMPLE 12

Expression of Oct4 in Porcine ES Cells, Injected into Mouse Blastocysts.

Figure 16A:
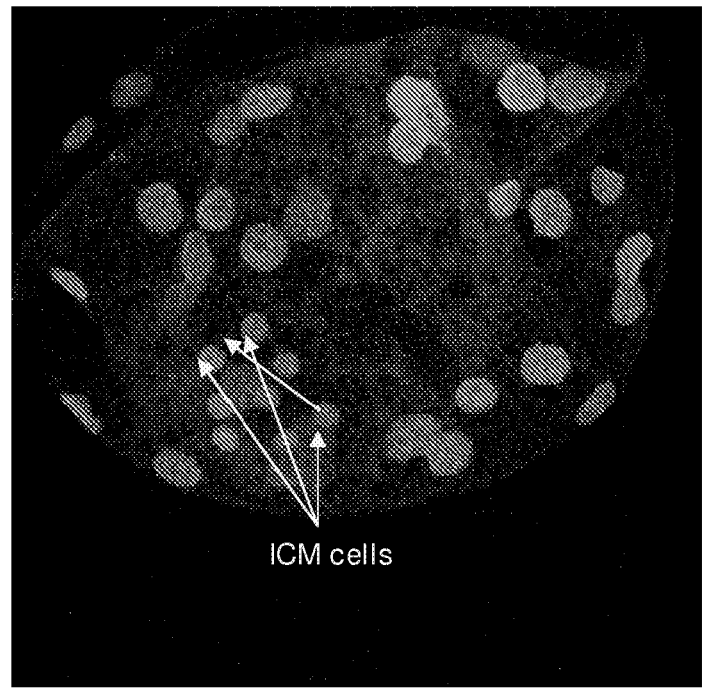
FIG. 16 shows Oct-4 expressions (green) in ICM cells (yellow arrows) of porcine blastocyst (Panel A) and in porcine blastocyst (Panel B) injected with porcine ES cells (red arrows).
Figure 16B:
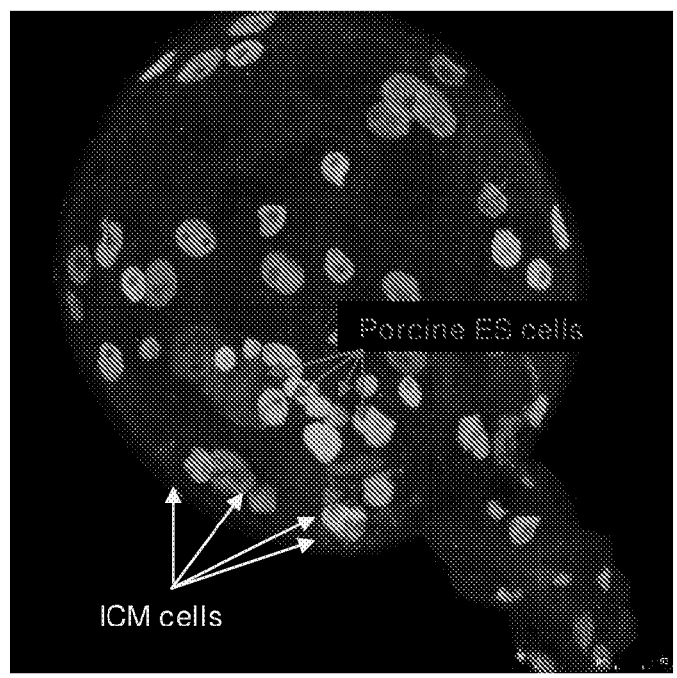

Porcine ES cells, isolated and maintained in culture for several passages as described in Example 5, were injected into Day 5 in vitro produced recipient porcine blastocysts, as described in Example 8. On the next day after injection shape restored blastocysts were examined for Oct 4 expression as described in Example 11. As shown at FIG. 16A, in porcine Day 6 non-injected blastocysts many cells of blastocysts express Oct-4, but ICM cell could be easy recognized by nuclei size. There are few ICM cells (yellow arrows) expressing Oct-4 and organized as disk. FIG. 16B represents hatching Day 6 porcine blastocysts, injected with porcine ES cells. Porcine ICM cells (yellow arrows) are organized in a more spread manner, whereas injected porcine ES cells (red arrows) are organized as a strip with accordance with how they were injected (see FIGS. 12A and 12B). Both types of cells express Oct-4, although porcine ES cells appear to have an elevated level (or ICM cell have reduced level) of Oct-4 expression.

Thus, the method of isolating pluripotent cells described herein provides an improvement in the ease and efficiency of isolation of pluripotent stem cells, by eliminating growth of extra-embryonic cells and the maintenance of the pluripotent stem cells in the undifferentiated states. In addition, the avoidance of the use of serum reduces the risk of contamination of cells with pathogens associated with serum.

Finally, it will be appreciated that various modifications and variations of the invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the art are intended to be within the scope of the present invention.

The invention claimed is:

1. A method of isolating a mammalian pluripotent embryonic stem cell from a mammalian pre-implantation embryo including one or more pluripotent embryonic stem cells, comprising the steps of:
   (i) selecting the mammalian pre-implantation embryo in a blastocyst stage of development;
   (ii) depressing, embedding or flattening all of the pre-implantation embryo into a feeder cell layer causing all cells of the embryo to make contact with the feeder cell layer;
   (iii) culturing the depressed, embedded or flattened pre-implantation embryo in a medium that is free of serum to (a) inhibit differentiation of the one or more pluripotent embryonic stem cells and allow undifferentiated growth of the one or more pluripotent embryonic stem cells resulting in formation of a homogeneous pluripotent embryonal outgrowth and (b) not allow growth of non-pluripotent cells from the pre-implantation embryo; and
   (iv) isolating a pluripotent embryonic stem cell from the one or more pluripotent embryonic stem cells.

2. The method of claim 1, wherein the medium includes a serum replacement and/or albumin.

3. The method of claim 2, wherein the medium includes 5 to 25% serum replacement.

4. The method of claim 1, wherein the method further comprises the step of establishing a homogeneous pluripotent primary culture of cells from the pre-implantation embryo, the primary culture including the one or more pluripotent embryonic stem cells.

5. The method of claim 1, wherein the feeder cell layer is treated to inhibit proliferation of the feeder cells.

6. The method of claim 1, wherein the zona pellucida of the pre-implantation embryo is removed prior to depressing, embedding or flattening all of the pre-implantation embryo into the feeder cell layer.

7. The method of claim 1, wherein the one or more pluripotent embryonic stem cells are cultured until the one or more pluripotent embryonic stem cells form a colony of cells.

8. The method of claim 7, wherein the colony is free of trophectoderm cells, differentiated cells and/or cells committed to differentiate.

9. The method of claim 1, wherein the blastocyst is a blastocyst produced in vitro or is a blastocyst derived in vivo.

10. The method of claim 1, wherein the medium includes L-glutamine, ribonucleosides, deoxyribonucleosides, sodium pyruvate, bFGF, hrEGF, 1X ITS, β-mercaptoethanol, non-essential amino acids and hrLIF.

11. A method of establishing a mammalian pluripotent embryonic stem cell line from a mammalian pre-implantation embryo, the method comprising the steps of:
   (i) isolating one or more pluripotent embryonic stem cells from the mammalian pre-implantation embryo including one or more pluripotent embryonic stem cells, comprising the substeps of:
      (A) selecting the mammalian pre-implantation embryo in a blastocyst stage of development;
      (B) depressing, embedding or flattening all of the pre-implantation embryo into a feeder cell layer causing all cells of the embryo to make contact with the feeder cell layer;
      (C) culturing the depressed, embedded or flattened pre-implantation embryo in a medium that is free of serum to (a) inhibit differentiation of the one or more pluripotent embryonic stem cells and allow undifferentiated growth of the one or more pluripotent embryonic stem cells resulting in formation of a homogeneous pluripotent embryonal outgrowth and (b) not allow growth of non-pluripotent cells from the pre-implantation embryo; and
      (D) isolating one or more pluripotent embryonic stem cells from the one or more pluripotent embryonic stem cells; and
   (ii) culturing the one or more isolated pluripotent embryonic stem cells in a medium that is free of serum to establish the pluripotent embryonic stem cell line.

12. A method of isolating a mammalian pluripotent embryonic stem cell from a mammalian pre-implantation embryo including one or more pluripotent embryonic stem cells, comprising the steps of:
   (i) selecting the mammalian pre-implantation embryo in a blastocyst stage of development;
   (ii) depressing, embedding or flattening all of the pre-implantation embryo into a feeder cell layer causing all cells of the embryo to make contact with the feeder cell layer;
   (iii) culturing the depressed, embedded or flattened pre-implantation embryo in a medium that is free of serum and comprises L-glutamine, ribonucleosides, deoxyribonucleosides, sodium pyruvate, bFGF, hrEGF, 1X ITS, β-mercaptoethanol, non-essential amino acids and hrLIF to (a) inhibit differentiation of the one or more pluripotent embryonic stem cells and allow undifferentiated growth of the one or more pluripotent embryonic stem cells resulting in formation of a homogeneous pluripotent embryonal outgrowth and (b) not allow growth of non-pluripotent cells from the pre-implantation embryo; and
   (iv) isolating a pluripotent embryonic stem cell from the one or more pluripotent embryonic stem cells.

13. A method of isolating a mammalian pluripotent embryonic stem cell from a mammalian pre-implantation embryo including one or more pluripotent embryonic stem cells, comprising the steps of:
   (i) selecting the mammalian pre-implantation embryo in a blastocyst stage of development;
   (ii) depressing, embedding or flattening all of the pre-implantation embryo into a feeder cell layer causing all cells of the embryo to make contact with the feeder cell layer;
   (iii) culturing the depressed, embedded or flattened pre-implantation embryo in a medium that is free of serum to (a) inhibit differentiation of the one or more pluripotent embryonic stem cells and allow undifferentiated growth of the one or more pluripotent embryonic stem cells resulting in formation of a homogeneous pluripotent embryonal outgrowth and (b) not allow growth of non-pluripotent cells from the pre-implantation embryo; and
   (iv) isolating a pluripotent embryonic stem cell from the one or more pluripotent embryonic stem cells;
wherein the one or more pluripotent embryonic stem cells are cultured until the one or more pluripotent embryonic stem cells form a colony of cells that is free of trophectoderm cells, differentiated cells and cells committed to differentiate.

14. A method of isolating a mammalian pluripotent stem cell from a mammalian pre-implantation embryo including one or more pluripotent stem cells, comprising the steps of:
   (i) selecting the mammalian pre-implantation embryo in a blastocyst stage of development;
   (ii) depressing, embedding or flattening all of the pre-implantation embryo into a feeder cell layer causing all cells of the embryo to make contact with the feeder cell layer;
   (iii) culturing the depressed, embedded or flattened pre-implantation embryo in a medium that is free of serum to (a) inhibit differentiation of the one or more pluripotent stem cells and allow undifferentiated growth of the one or more pluripotent stem cells resulting in formation of a homogeneous pluripotent embryonal outgrowth and (b) not allow growth of non-pluripotent cells from the pre-implantation embryo; and
   (iv) isolating a pluripotent stem cell from the one or more pluripotent stem cells.

15. A method of isolating a mammalian pluripotent embryonic stem cell from a mammalian pre-implantation embryo including one or more pluripotent embryonic stem cells, comprising the steps of:
   (i) selecting the mammalian pre-implantation embryo in a blastocyst stage of development;
   (ii) depressing, embedding or flattening all of the pre-implantation embryo into a feeder cell layer causing all cells of the embryo to make contact with the feeder cell layer;
   (iii) culturing the depressed, embedded or flattened pre-implantation embryo in a medium that is free of serum to (a) inhibit differentiation of the one or more pluripotent embryonic stem cells and allow undifferentiated growth of the one or more pluripotent embryonic stem cells resulting in formation of a homogeneous pluripotent embryonal outgrowth and (b) not allow growth of non-pluripotent cells from the pre-implantation embryo; and (iv) isolating a pluripotent embryonic stem cell from the one or more pluripotent embryonic stem cells;

wherein the isolated pluripotent embryonic stem cell is free of non-apoptotic non-pluripotent cells derived from the embryo.

* * * * *